United States Patent [19]

Shaw

[11] Patent Number: 6,001,817
[45] Date of Patent: Dec. 14, 1999

[54] PHARMACEUTICAL COMPOSITION COMPRISED OF CISPLATIN, AND PROCESSES FOR MAKING AND USING SAME

[75] Inventor: Jiajiu Shaw, Ann Arbor, Mich.

[73] Assignee: Unitech Pharmaceuticals, Inc., Ann Arbor, Mich.

[21] Appl. No.: 09/005,523

[22] Filed: Jan. 12, 1998

[51] Int. Cl.$^6$ .................................................. A01N 43/04
[52] U.S. Cl. ................................ 514/45; 514/46; 514/47; 514/48; 514/49; 514/50; 514/51; 514/19; 514/885; 536/26.7; 536/26.8; 536/27.6; 536/27.81; 536/28.5; 536/28.53; 536/28.54
[58] Field of Search .................................. 514/45, 46, 47, 514/49, 50, 51, 19; 536/26.7, 26.8, 27.6, 27.81, 28.5, 28.53, 28.54

[56] References Cited

U.S. PATENT DOCUMENTS 4,207,416  6/1980  Hoeschele .
5,466,678  11/1995  Kawabata et al. .
5,529,775  6/1996  Mikulski et al. .

OTHER PUBLICATIONS

Hollis et al., J. Med Chem., vol. 32, No. 1, pp. 128–136 (1989).

Peresie et al., Inorganica Chimica Acta, vol. 29, pp. L247–L248, (1978).

*Primary Examiner*—James O. Wilson
*Attorney, Agent, or Firm*—Brinks Hofer Gilson & Lione

[57] ABSTRACT

A pharmaceutical composition, comprising cisplatin, a special carrier and, optionally, customary pharmaceutical excipients, is disclosed. The preparation of this pharmaceutical composition is also disclosed. The composition may be used to treat cancer and Acquired Immune Deficiency Syndrome (AIDS).

6 Claims, No Drawings

PHARMACEUTICAL COMPOSITION COMPRISED OF CISPLATIN, AND PROCESSES FOR MAKING AND USING SAME

BACKGROUND OF THE INVENTION

Cisplatin (cis-diamminedichloroplatinum, cis-Pt(NH$_3$)$_2$Cl$_2$, molecular weight 300.05) has been used as a chemotherapeutic agent for many years since the discovery of its anti-tumor activity by B. Rosenberg et al. (*Nature,* 1965, 205, 698;*Nature,* 1972, 222, 385).

After so many years, cisplatin is still being widely used because of its efficacy. It has been used to treat cancer patients for head, neck, ovarian cancer, etc. However, its major drawback, the toxicity, is still a big concern.

Many attempts have been made to modify the cisplatin molecule in order to reduce its toxicity; many other attempts have been made to understand the interaction between cisplatin and DNA, which is the ultimate target of cisplatin. A few attempts have also been made to modify the composition of cisplatin dosage form to reduce its toxicity or improve its efficacy.

In terms of modifying the cisplatin molecule, many people have attempted to change the ligand or ligands on Platinum. Examples of the modifications on cisplatin have been made by K. C. Tsou, et al.(*J Clin. Hemat. Oncol.* 1977, 7, 322,), R. J. Speeder et al. (*J. Clin. Hemat. Oncol.* 1977, 7, 210), A. Mathew et al. (*Chem. Comm.* 1979, 222), D. Rose, et al. (*Cancer Treatment Reviews,* 1985, 12, 1), and D. Alberts et al. (*Cancer Treatment Reviews,* 1985, 12, 83).

In terms of understanding the interaction between cisplatin and DNA, the X-ray structure of the adduct of cisplatin and DNA was determined by S. E. Sherman et al. (*Science* 1985, 230, 412). This critical work provides a clear insight as to how cisplatin may function as an inhibitor to stop the DNA replication process, thus, kill the cell eventually. Their studies show that cisplatin binds to synthetic oligodeoxynucleotides to form cis-[Pt(NH$_3$)$_2${d(pGpG)}], where "d(pGpG)" represents dinucleotide made of deoxyguanosine monophosphate. They indicated that the intrastrand cross-linked cis-[Pt(NH$_3$)$_2${d(pGpG)}] is a very possible reason why cisplatin is capable of inhibiting DNA replication. Fichtinger-Schepman et. al., (*Biochemistry,* 1985, 24, 707–713) synthesized and identified four adducts of cisplatin and DNA residues. They are: cis-[Pt(NH$_3$)$_2$d(pGpG)], cis-[Pt(NH$_3$)$_2$d(pApG)], cis-[Pt(NH$_3$)$_3$dGMP], and cis-[Pt(NH$_3$)$_2$(dGMP)$_2$], where "d(pGpG)" represents dinucleotide made of deoxyguanosine monophosphate, "d(pApG)" represents dinucleotide made of deoxyadenosine monophosphate and deoxyguanosine monophosphate, and dGMP represents deoxyguanosine monophosphate.

The most common binding of cisplatin to DNA is through the loss of chloride ion to form Pt-N bond to the N$_7$ of guanine on deoxyguanosine. Most references indicate that N$_7$ of guanine is the major binding site for guanosine nucleotide. Examples of the references are F. J. Dijt et al. (*J Am. Chem. Soc.* 1984, 106, 3644–3647), A. M. J. Fichtinger-Schepman et al. (*Biochemistry* 1985, 24, 707–713), and S. E. Sherman et al. (*Science* 1985, 230, 412–417). However, other nucleosides or deoxynucleosides are also known to bind cisplatin (chapter 9, *Metal-DNA Chemistry,* 1989, American Chemical Society Symposium Series 402, 119–145).

In terms of modifying the composition of the dosage forms of cisplatin, many articles were published. Cisplatin has been used in combination with caffeine by H. Yasutake et al. (*Gan to Kagaku Ryoho* 1989, 16, 2031–8) and by H. Tsuchiya (*Kanazawa Daigaku Juzen Igakkai Zasshi* 1988, 97, 543–56). Cisplatin has also been used in combination with cytosine arabinoside and the combination has shown some advantages as shown by J. Berek et al. (*Obstet. Gynecol.* 1989, 74, 663–6). Another combination, cisplatin and novobiocin, has also been shown to be advantageous by P. Eder et al. (Cancer Research 1989, 49, 595–8. A patent issued in 1992 (U.S. Pat. No. 5,130,145) was related to this invention. This prior art indicates that when cisplatin and L-ascorbic acid are administered simultaneously, the anti-tumor activity is higher.

None of these prior arts uses nucleoside or deoxynucleoside along with cisplatin in a pharmaceutical composition for cancer therapy. The main reason for this is that nucleosides and deoxynucleosides have not been used as pharmaceutical excipients.

This invention comprises a pharmaceutical composition comprising cisplatin, a special carrier, and, optionally, customary pharmaceutical excipients, whereas said special carrier represents one to four nucleosides, one to four deoxynucleosides, or the combination of one to four nucleosides and one to four deoxynucleosides, wherein nucleoside represents adenosine, guanosine, cytidine, or uridine and deoxynucleoside represents deoxyadenosine, deoxyguanosine, deoxycytidine, or thymidine. Said pharmaceutical excipients are customary and physiologically acceptable pharmaceutical excipients such as mannitol, lactose, sodium chloride, phosphates, water, ethanol, hydrochloric acid, magnesium stearate, cellulose, starch, polyethylene glycol, etc. Therefore, the composition may be in a liquid or solid dosage form suitable for parenteral or oral administration to a patient.

This composition is different from the conventional pharmaceutical compositions which do not contain nucleosides or deoxynucleosides.

Based on the studies of R. A. Lerner et al. (*Proc. Natl. Acad. Sci. USA,* 1971, 68, 1212), J. C. Rogers et al. (*J. Immunol.* 1981, 126, 703), J. Woo et al. (*Biochem. J.* 1972, 128, 1273), and D. A. Juckett et al. (*Cancer Research* 1982, 42, 3565), it was shown that most cancer cells have DNA or RNA sticking out of the cells. Because nucleosides or deoxynucleosides are the building blocks of RNA or DNA, it is conceivable that a drug molecule comprising available nucleoside or deoxynucleoside may be more likely to be grabbed by the DNA or RNA sticking on the outside of the cancer cells, thus, giving the drug molecule better opportunity to attack the cancer cells.

Because the preparation of this composition comprises mixing cisplatin and nucleoside or deoxynucleoside in a suitable solvent for a significant period of time, it contains some of the adducts formed between cisplatin and nucleoside or deoxynucleoside. These adducts may have stronger affinity to the DNA or RNA being replicated. Since most cancer cells are much more active in reproducing DNA or RNA, it can become a more likely target for the adduct formed between cisplatin and nucleoside or deoxynucleoside. As a result, this composition may be less toxic than cisplatin alone or cisplatin in other pharmaceutical compositions. The in-vitro results indicate that it is the case for the cisplatin/guanosine 1:1 adduct as shown in previous patent application (application Ser. No. 08/818,444).

Predominantly, cisplatin binds onto deoxyguanosine of DNA. However, cisplatin also binds onto other deoxynucleosides or nucleosides. Thus, nucleosides or deoxynucleosides, other than guanosine and deoxyguanosine, may also show similar effects in reducing the toxicity of cisplatin even though their affinity to cisplatin may not be as strong as that of guanosine or deoxyguanosine.

Therefore, this invention is a better pharmaceutical composition than other cisplatin compositions.

Because cisplatin binds onto DNA or RNA, this composition may also be used to treat viruses, such as Human Immunodeficiency Virus (HIV), to bind its DNA or RNA and kill the virus. Thus, the composition may be used for the treatment of Acquired Immune Deficiency Syndrome (AIDS) patient. The composition may also be used in combination with other well known AIDS drugs, such as 3'-azidothymidine (AZT), to interfere with the HIV enzyme reverse transcriptase and achieve the goal of hampering the reproduction of HIV.

DETAILED DESCRIPTION OF THE INVENTION

This invention comprises a novel pharmaceutical composition comprising cisplatin, a special carrier, and, optionally, customary pharmaceutical excipients. Said pharmaceutical composition has a mole ratio between cisplatin and said special carrier in the range of 1:0.1 to 1:2, preferably 1:0.5 to 1:1.5, most preferably 1:0.8 to 1:1.2. Said special carrier comprises one to four nucleosides, one to four deoxynucleosides, or the combination of one to four nucleosides and one to four deoxynucleosides, wherein nucleoside represents adenosine, guanosine, cytidine, or uridine and deoxynucleoside represents deoxyadenosine, deoxyguanosine, deoxycytidine, or thymidine. Said excipients are customary and physiologically acceptable pharmaceutical excipients, such as mannitol, lactose, sodium chloride, phosphates, water, ethanol, hydrochloric acid, magnesium stearate, cellulose, starch, polyethylene glycol, etc.

The method of preparing the composition comprises the following:

(1) Weigh a suitable amount of cisplatin and a suitable amount of the special carrier, according to the previous paragraph, in a suitable solvent so that the percentage of cisplatin is 0.005% to 0.25% in the aliquot, whereas said suitable solvent is water, methanol, ethanol, acetone, 0.1% to 99% methanol in water, 0.1% to 99% ethanol in water, 0.1% to 99% acetone in water, 0.05% to 5.0% sodium chloride in water, 0.0001 N to 1.0 N hydrochloric acid, or the mixture of said solvents.

(2) Stir the aliquot overnight or until it becomes a solution.

(3) Filter through a suitable filter with a porosity of between 0.1 $\mu$m to 1.0 $\mu$m, preferably between 0.2 $\mu$m to 0.45 $\mu$m.

(4) Optionally, dry the filtrate from step (3) under vacuum or by other standard pharmaceutical techniques.

(5) Optionally, the dried composition from step (4) is reconstituted to a solution or a suspension by a suitable solvent so that the percentage of cisplatin is 0.005% to 0.25%, preferably 0.01% to 0.1%, whereas said suitable solvent comprises water, ethanol, 0.1% to 90% ethanol in water, 0.05% to 5.0% sodium chloride in water, 0.0001 N to 1.0 N hydrochloric acid, or the mixture of said solvents.

(6) Optionally, the dried composition from step (4) is blended with suitable amounts of physiologically acceptable pharmaceutical excipients and be encapsulated or compressed into capsules or tablets by utilizing standard pharmaceutical techniques.

Note: Said process in step (1), cisplatin and the special carrier may be placed and mixed in two individual containers, each containing said solvent, to make two aliquots; the two aliquots are then mixed together in a container before proceeding to step (2).

Several examples of the composition and the preparation are shown as follow:

EXAMPLE 1

1. Weigh 100 mg of cisplatin (about 0.33 mmole).
2. Weigh 94 mg of Guanosine (about 0.33 mmole).
3. Add the weighed cisplatin and guanosine into 350 mL of water.
4. Stir the aliquot overnight or until it becomes a solution.
5. Filter the solution through a suitable filter with a porosity of 0.2 $\mu$M and collect the filtrate. The final composition has a cisplatin concentration of about 0.029% and the mole ratio of cisplatin and guanosine is about 1:1.

EXAMPLE 2

1. Weigh 100 mg of cisplatin (about 0.33 mmole) and add it into 200 mL of water.
2. Weigh 71 mg of Guanosine (about 0.25 mmole) and 67 mg of deoxyguanosine (about 0.25 mmole); add both into 200 mL of water.
3. Mix the two aliquots from step 1 and from step 2 in a suitable container.
4. Stir the aliquot (from step 3) overnight or until it becomes a solution.
5. Filter the solution through a suitable filter with a porosity of 0.2 $\mu$M and collect the filtrate.
6. Dry the filtrate by a rotary evaporator or other standard pharmaceutical techniques. The final composition has a mole ratio of about 1:1.5 between cisplatin and (guanosine+deoxyguanosine).

EXAMPLE 3

1. Add the solid composition from step 6 of Example 2 into 200 mL of 0.5% sodium chloride and mix until it becomes a solution.
2. Filter the solution through a suitable filter with a porosity of 0.2 $\mu$M and collect the filtrate. The final concentration of cisplatin is about 0.05% and the mole ratio of cisplatin and (guanosine+deoxyguanosine) is about 1:1.5.

EXAMPLE 4

1. Weigh 100 g of the dry composition made according to the procedures in Example 2; add it into 300 g of lactose; mix till the blend is uniform.
2. Add the blend made from step 1 into 400 g of mannitol and mix well.
3. Add 10 g of magnesium stearate into the blend made from step 2 and mix for three minutes.
4. Encapsulate the blend from step 3 into suitable capsules so that each capsule contains 100 mg of cisplatin.

The final composition in each capsule contains 100 mg cisplatin and the mole ratio between cisplatin and (guanosine+deoxyguanosine) is about 1:1.5.

Another part of this invention is related to the method for treating cancer patients by this composition. The composition may be administered to a cancer patient orally, or by subcutaneous or intravenous injection, or by means of an implanted reservoir, or by means of applying on the cancerous skin.

The injectable compositions are normally in the form of an aqueous solution. If necessary, pharmaceutically-acceptable suspension may be employed. Typically, such a solution contains cisplatin at a concentration of 0.005%–0.25% (0.05 mg/mL–2.5 mg/mL), more commonly 0.01%–0.1% (0.1 mg/mL–1 mg/mL). The dosage administered by injection comprises cisplatin in the range of 5–1,000 mg in the first day of every 1–4 weeks depending upon the patient. Typically, one might administer a dosage of 50–400 mg in the first day of every 1–4 weeks to a patient having a body weight of 40–100 kg, although in appropriate cases such dosages may prove useful for patients having a body weight outside this range.

The composition may also be administered orally, for example, as a solution or a suspension or as tablets or capsules. Solution and suspension for oral administration are typically of about the same concentration as those used for injection. However, when administering the drug orally, it may be desirable to use a higher dosage rate than when administering it by injection. For example, a dosages containing 10–1,500 mg cisplatin in the first day of every 1–4 weeks may be used. Typically, one might administer a dosage containing 50–600 mg cisplatin in the first day of every 1–4 weeks. In preparing such tablets or capsules, standard tablet or capsule making techniques may be employed. If desired, suitable pharmaceutically acceptable excipients such as starch, mannitol, cellulose or lactose may be used in preparing the tablets or capsules. Capsules may also be prepared using soft gelatin as the encapsulating agent. If desired, such capsules may be in the form of sustained release capsules wherein the main capsule contains microcapsules which release the active ingredient over a period of several hours.

This composition may also be used in the treatment of AIDS. Because of the ability of cisplatin to hamper the DNA or RNA replication process, it is likely that this composition will also be effective against the HIV and may be used for the treatment of AIDS. It may also be used in combination with other well known AIDS drugs, including but not limited to AZT, to interfere with the HIV enzyme reverse transcriptase and achieve better results.

This composition may be administered to an AIDS patient in the same way as in the treatment of a cancer patient. A composition having 10–600 mg of cisplatin in the first day of every 1–4 weeks may be administered.

When used in conjunction with a well known drug for AIDS, such as AZT, the dosage of cisplatin in the composition may be suitably reduced. A composition having 5–1,500 mg of cisplatin in the first day of every 1–4 weeks may be administered; the dosage and the method of administration of said drug for AIDS is the same as it is normally used.

SUMMARY, RAMIFICATION, AND SCOPE

In conclusion, this invention comprises a novel pharmaceutical composition of cisplatin, the preparation, and the use of said composition for the treatment of cancer and AIDS.

Although the description above contains many specificities, these should not be construed as limiting the scope of the invention but as merely providing the illustrations of some of the presently preferred embodiments of this invention.

Thus the scope of this invention should be determined by the appended claims and their legal equivalents, rather than by the examples given.

I claim:

1. A method of preparing a pharmaceutical composition which comprises a cisplatin complex comprising (i) cisplatin and (ii) a special carrier comprising adenosine, guanosine, cytidine, uridine, deoxyadenosine, deoxyguanosine, deoxycytidine, or thymidine, or mixtures thereof; and at least one excipient; wherein said pharmaceutical composition has a molar ratio between said cisplatin complex and said special carrier in the range of 1:0.1 to 1:2, said method comprising:

weighing cisplatin and the special carrier in a solvent, which is water, methanol, ethanol, acetone, 0.1% to 99% by volume methanol in water, 0.1 to 99% by volume acetone in water, 0.05% to 5.0% by weight sodium chloride in water, or 0.0001 to 1.0 N hydrochloric acid, or a mixture thereof, to form an aliquot so that the percentage of cisplatin is 0.005% to 0.25% by weight in the aliquot, stirring the aliquot overnight or until it becomes a solution, filtering through a filter with a porosity of between 0.1 $\mu$m, and drying the filtrate.

2. The method of claim 1, wherein the cisplatin and the special carrier are placed in two individual containers with solvent and subsequently mixed together to obtain a solution containing 0.005 to 0.25% by weight of cisplatin.

3. The method of claim 1, further comprising reconstituting the dried filtrate with solvent to obtain a solution containing 0.005 to 0.25% by weight of cisplatin.

4. The method of claim 1, further comprising blending the dried filtrate is with a pharmaceutical excipient and encapsulating or compressing the blend into capsules or tablets.

5. A method of treating Acquired Immune Deficiency Syndrome (AIDS), comprising administering a pharmaceutical composition either orally or parenterally to an AIDS patient one day every 1–4 weeks;

wherein said pharmaceutical composition which comprises a cisplatin complex comprising (i) cisplatin and (ii) a special carrier comprising adenosine, guanosine, cytidine, uridine, deoxyadenosine, deoxyguanosine, deoxycytidine, or thymidine, or mixtures thereof; and at least one excipient; wherein said pharmaceutical composition has a molar ratio between said cisplatin complex and said special carrier in the range of 1:0.1 to 1:2 and pharmaceutical composition has 10–600 mg of cisplatin.

6. A method of treating Acquired Immune Deficiency Syndrome (AIDS), comprising administering azidothymidine (AZT), and concurrently administering a pharmaceutical composition either orally or parenterally to an AIDS patient one day every 1–4 weeks;

wherein said pharmaceutical composition which comprises a cisplatin complex comprising (i) cisplatin and (ii) a special carrier comprising adenosine, guanosine, cytidine, uridine, deoxyadenosine, deoxyguanosine, deoxycytidine, or thymidine, or mixtures thereof; and at least one excipient; wherein said pharmaceutical composition has a molar ratio between said cisplatin complex and said special carrier in the range of 1:0.1 to 1:2 and pharmaceutical composition has 5 to 1,500 mg of cisplatin.

* * * * *

UNITED STATES PATENT AND TRADEMARK OFFICE
CERTIFICATE OF CORRECTION

PATENT NO. : 6,001,817  
DATED : December 14, 1999  
INVENTOR(S) : Jiajiu Shaw

Page 1 of 1

It is certified that error appears in the above-identified patent and that said Letters Patent is hereby corrected as shown below:

<u>Column 6,</u>  
Lines 18-19, delete "0.1 μm, and" and substitute -- 0.1 μM to 1.0 μM and -- in its place.

Signed and Sealed this

Seventh Day of May, 2002

*Attest:*

JAMES E. ROGAN  
*Attesting Officer*     *Director of the United States Patent and Trademark Office*